United States Patent
Klokkerud et al.

(10) Patent No.: US 8,902,416 B2
(45) Date of Patent: Dec. 2, 2014

(54) APPARATUS AND METHOD FOR INSPECTING MATTER

(75) Inventors: Arne Klokkerud, Son (NO); Martin Kermit, Oslo (NO); Ole Onsrud, Rasta (NO)

(73) Assignee: Tomra Sorting AS, Asker (NO)

( * ) Notice: Subject to any disclaimer, the term of this patent is extended or adjusted under 35 U.S.C. 154(b) by 0 days.

(21) Appl. No.: 13/825,420

(22) PCT Filed: Sep. 19, 2011

(86) PCT No.: PCT/NO2011/000260
§ 371 (c)(1),
(2), (4) Date: May 13, 2013

(87) PCT Pub. No.: WO2012/039622
PCT Pub. Date: Mar. 29, 2012

(65) Prior Publication Data
US 2013/0222806 A1    Aug. 29, 2013

(30) Foreign Application Priority Data
Sep. 24, 2010 (NO) .................................. 20101332

(51) Int. Cl.
| | |
|---|---|
| *G01N 21/47* | (2006.01) |
| *G01N 21/27* | (2006.01) |
| *G01N 21/49* | (2006.01) |
| *G02B 26/12* | (2006.01) |
| *G01N 21/85* | (2006.01) |

(52) U.S. Cl.
CPC .......... *G01N 21/4738* (2013.01); *G01N 21/278* (2013.01); *G01N 21/85* (2013.01); *G01N 21/49* (2013.01); *G01N 21/4785* (2013.01); *G02B 26/124* (2013.01)
USPC ....................................... 356/237.1; 356/246

(58) Field of Classification Search
CPC .......... G01N 21/4738; G01N 21/4783; G01N 21/278; G01N 21/49; G01N 21/85; G02B 26/124
USPC ............................ 356/445, 446, 237.1–237.5
See application file for complete search history.

(56) References Cited

U.S. PATENT DOCUMENTS

| | | |
|---|---|---|
| 3,786,266 A | 1/1974 | Reid et al. |
| 4,283,147 A * | 8/1981 | Dreyfus et al. ............... 356/445 |

(Continued)

FOREIGN PATENT DOCUMENTS

| | | |
|---|---|---|
| DE | 4207760 A1 | 9/1993 |
| EP | 0721126 A1 | 7/1996 |
| WO | 2005106438 A1 | 11/2005 |

OTHER PUBLICATIONS

Norwegian Search Report in related Norwegian Application No. 20101332, dated Apr. 8, 2011.

*Primary Examiner* — Sang Nguyen
(74) *Attorney, Agent, or Firm* — Buchanan Ingersoll & Rooney P.C.

(57) ABSTRACT

The present invention relates to an apparatus (10) for inspecting matter (12), the apparatus comprising: an emitting device (14) adapted to emit radiation; a stop element (20) adapted to block some (16a) of the radiation emitted by the emitting device; a scanning device (26) adapted to project a dark area (24) caused by the stop element on the matter, and to redirect radiation (16b) having passed the stop element towards the matter, wherein at least some of the redirected radiation is scattered within the matter and passes out of the matter as scattered radiation (42); and a detection device (34) adapted to receive or detect the scattered radiation via the scanning device, wherein the detection device's field of view (36) coincides with the projected dark area (24). The present invention also relates to a corresponding method.

14 Claims, 8 Drawing Sheets

(56) References Cited

U.S. PATENT DOCUMENTS

| | | |
|---|---|---|
| 4,600,105 A | 7/1986 | Van Zyl et al. |
| 4,730,932 A | 3/1988 | Iga et al. |
| 4,737,650 A * | 4/1988 | West .................. 250/559.07 |
| 5,241,329 A * | 8/1993 | Guerin ..................... 347/233 |
| 5,448,359 A * | 9/1995 | Schick et al. ............. 356/609 |
| 5,559,627 A * | 9/1996 | Harris et al. ............. 359/216.1 |
| 5,615,038 A * | 3/1997 | Suzuki et al. ............ 359/210.1 |
| 5,675,419 A | 10/1997 | Van Den Bergh et al. |
| 5,894,345 A | 4/1999 | Takamoto et al. |
| 5,917,590 A * | 6/1999 | Greve .................. 356/237.3 |
| 5,945,685 A | 8/1999 | Imaino et al. |
| 6,438,396 B1 | 8/2002 | Cook et al. |
| 6,473,168 B1 * | 10/2002 | Ruymen .................. 356/237.2 |
| 7,768,629 B2 * | 8/2010 | Typpo et al. ............. 356/4.01 |
| 8,564,766 B2 * | 10/2013 | Berghmans ............. 356/237.3 |
| 2008/0018892 A1 * | 1/2008 | Haugholt et al. ......... 356/318 |
| 2008/0304040 A1 * | 12/2008 | Greenberg et al. ....... 356/4.01 |
| 2010/0128221 A1 | 5/2010 | Muller et al. |

\* cited by examiner

APPARATUS AND METHOD FOR INSPECTING MATTER

TECHNICAL FIELD

The present invention relates to an apparatus and method for inspecting matter, for instance for inspecting a stream of organic objects such as meat, chicken, and/or fish.

BACKGROUND

WO2005106438A1 (TITECH VISIONSORT AS) relates to an apparatus and method for inspecting a stream of matter by light scattering inside the matter. FIG. 1 in WO2005106438A1 discloses a system comprising a probe including an emitting device which emits a detection medium in the form of beams of electromagnetic radiation of a substantially constant intensity which are incident to some matter, which has a variety of lamina variations within its body. Once the incident beams reach the surface of the matter, some of the radiation penetrates the surface of the matter and is scattered within the matter and varied by the lamina variations within the matter. The scattered varied medium then passes out of the matter through the top surface as rays, a portion of which rays are focused using a lens, onto a detection device for generating detection data in dependence upon the varied radiation. However, the system in FIG. 1 in WO2005106438A1 is a point measuring device, and it needs a fixed distance between the matter and the lens.

Further, FIGS. 2-3 in WO2005106438A1 discloses a system for automatically inspecting a stream of matter for varying composition, comprising a row of lamps serving to emit a detection medium via a focusing cylindrical mirror to an irradiated zone of the stream at which the medium penetrates a surface of the matter, the irradiated zone extending continuously across substantially the width of the stream, a rotary polygonal mirror for receiving the varied medium emanating from the matter via a cylindrical lens at a detection zone, and a detecting device serving to generate detection data in dependence upon the varied medium. The system further comprises a blackened metallic screen for suppression of stray radiation. However, when the height of the matter varies beyond the lamps' focus on the matter, reflection detection will occur rather than transflection, which will negatively affect the inspection. Further, the screen physically limits the height of matter to be inspected.

BRIEF SUMMARY

It is an object of the present invention to at least partly overcome the above problems, and provide an improved apparatus and method for inspecting matter.

This object, and other objects that may appear from the following description, is achieved by an apparatus and method according to the appended independent claims. Embodiments are set forth in the appended dependent claims.

According to an aspect of the invention, there is provided an apparatus for inspecting matter, the apparatus comprising: an emitting device adapted to emit radiation; a stop element adapted to block some of the radiation emitted by the emitting device; a scanning device adapted to project a dark area cased by the stop element onto the matter, and to redirect radiation having passed the stop element towards the matter, wherein at least some of the redirected radiation is scattered within the matter and passes out of the matter as scattered radiation (transflection); and a detection device adapted to receive or detect the scattered radiation via the scanning device, wherein the detection device's field of view coincide with the projected dark area.

Due to the stop element and the corresponding placement of the detection device, no radiation reflected by the surface of the matter will be received by the detection device, and any height variation of the matter is no longer critical with respect of surface reflection. No optical lens for focusing the scattered radiation towards the detection device is necessary nor present. Further, the scanning device allows the provision of a rather wide inspection zone.

The stop element is preferably provided in front of the emitting device. Said stop element may be provided in an aperture placed in front of the emitting device. By means of this arrangement, the radiation pattern ultimately reaching the matter may be accurately defined.

The emitting device and the detection device may be obliquely arranged in relation to each other. This facilitates placement of the emitting and detection devices in the apparatus, as they will not obstruct each other.

The scanning device may be adapted to sweep the projected dark area, the redirected radiation, and the field of view of the detection device along an inspection width where matter to be inspected may be present. The scanning device may for instance be a rotatable or rotating polygonal mirror having a plurality of sides.

At least one side of the rotatable polygonal mirror may comprise a calibration element. Said calibration element may be one of: a white calibration element including at least one substantially white surfaces angled for allowing the detection device to directly receive or detect radiation reflected by the substantially white surface(s); and a spectral calibration element including two reflecting surfaces angled (e.g. orthogonal) in relation to each other and with a transmission object provided there between, the transmission object having a particular spectral signature. The provision of at least one calibration element on the rotatable polygonal mirror allows for automatic and repeated, almost continuous, calibration during use of the present apparatus. The present apparatus may comprise two such calibration elements (suitably one white calibration element and one spectral calibration element) arranged on opposite sides of the rotatable polygonal mirror. Such a configuration balances the weight of the rotatable polygonal mirror.

The present apparatus may further comprise a conveyor adapted to convey matters to be inspected.

The apparatus may further comprise a beam splitter arranged in an optical path between the scanning device and the detection device, wherein the beam splitter is adapted transmit some of the radiation incoming towards it to the detection device and to reflect some of the incoming radiation to another detection device. The beam splitter may be tilted or tiltable, such that the another detection device may receive radiation reflected by the matter.

According to another aspect of the invention, there is provided a method for inspecting matter, which method comprises: emitting radiation by means of an emitting device; blocking some of the emitted radiation by means of a stop element provided in front of the emitting device; by means of a scanning device, projecting a dark area caused by the stop element on the matter, and redirecting radiation having passed the stop element towards the matter, wherein at least some of the redirected radiation is scattered within the matter and passes out of the matter as scattered radiation; and receiving or detecting by means of a detection device the scattered radiation via the scanning device, wherein the detection device's field of view coincides with the projected dark area.

This aspect may exhibit the same or similar features and technical effects as the previously described aspect of the invention.

BRIEF DESCRIPTION OF THE DRAWINGS

These and other aspects of the present invention will now be described in more detail, with reference to the appended drawings showing a currently preferred embodiments of the invention.

FIG. 8b is a side view of the detection device of FIG. 8a.

DETAILED DESCRIPTION

Figure 1:
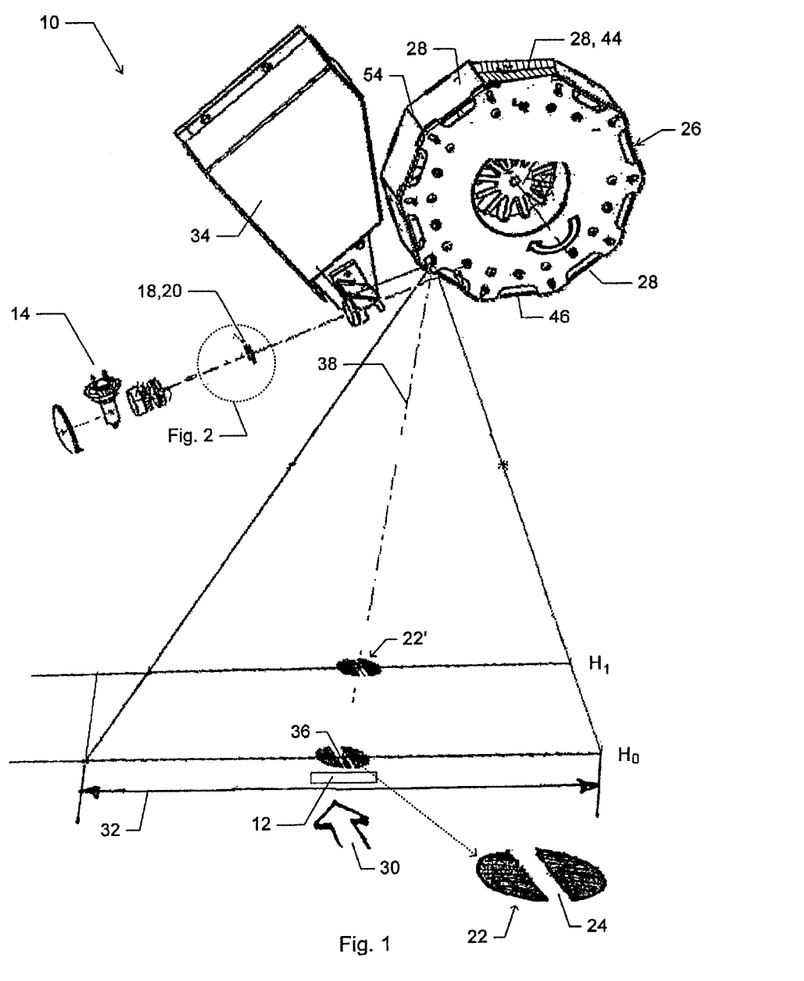
FIG. 1 is a perspective view of an apparatus for inspecting matter according to an embodiment of the present invention.
Figure 1A:
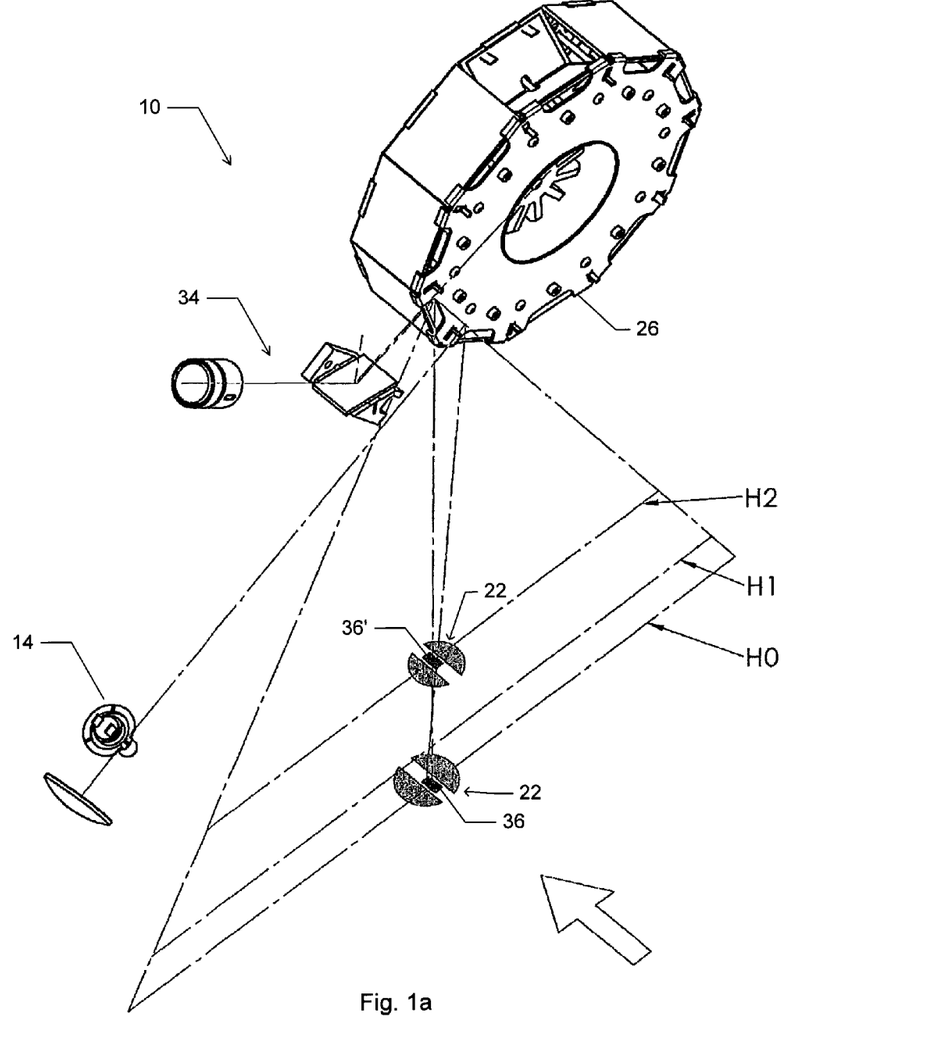
FIG. 1a is another perspective view of the apparatus of FIG. 1.
Figure 1B:
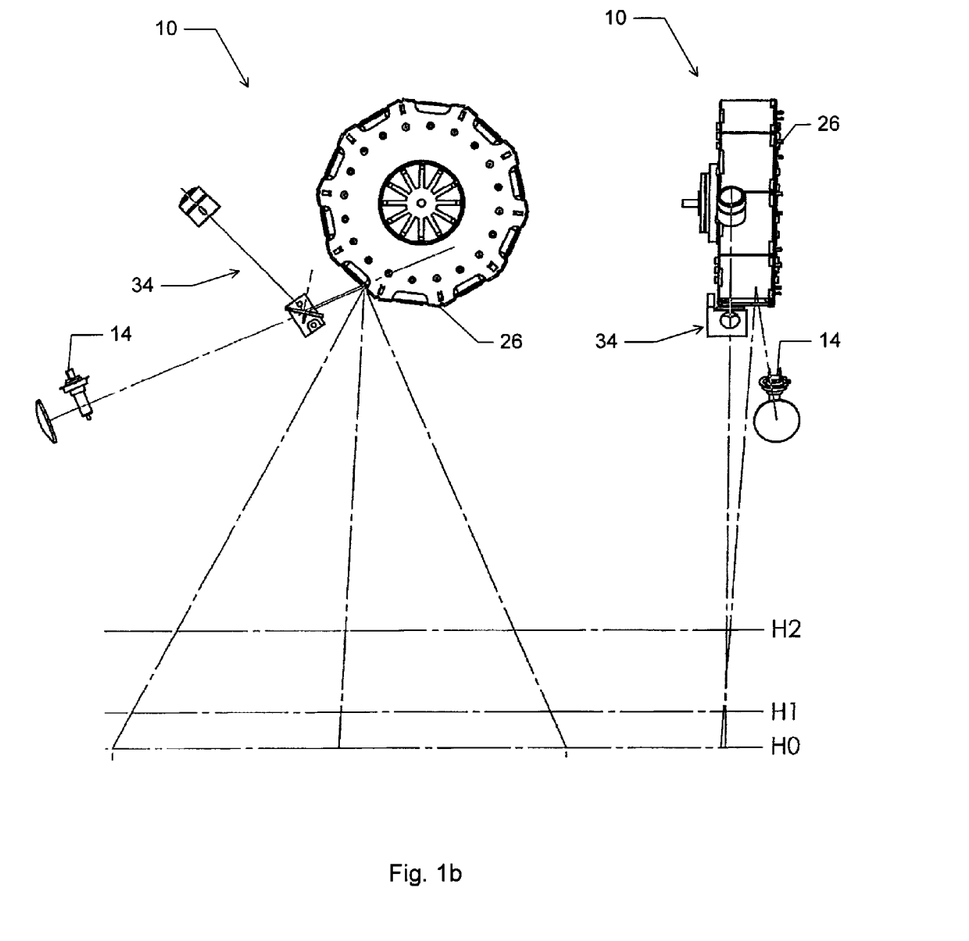
FIG. 1b are two side views of the apparatus of FIG. 1.

FIG. 1 is a perspective view of an apparatus 10 for inspecting matter 12 according to an embodiment of the present invention. The apparatus 10 is also shown in FIGS. 1a-1b.

The apparatus 10 comprises an emitting device 14. The emitting device 14 may for instance be a halogen lamp module. The radiation or light emitted by the emitting device 14 may be infrared (IR) radiation, though other wavelengths can also be used, such as visible light or ultraviolet (UV) light.

Figure 2:
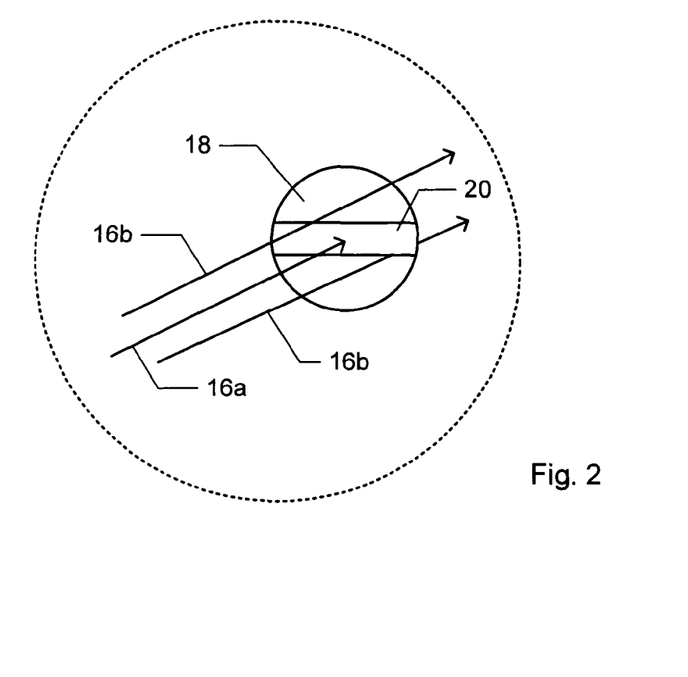
FIG. 2 is a detailed view of an aperture of the apparatus in FIG. 1.

In front of the emitting device 14, there is placed an aperture 18, see also FIG. 2. The aperture 18 is substantially circular, and provided with a stop element 20 shaped like a band or rectangle intersecting the aperture 18 along its diameter. The stop element 20 is adapted to block the radiation 16a emitted by the emitting device 14, while other radiation 16b emitted by the emitting device 14 may pass the aperture 18. Any wider radiation emitted by the emitting device 14 may be prevented from passing the aperture 18. The light may be focused by means of a front lens. The resulting radiation output as projected on the matter 12 is illustrated enlarged by 22 in FIG. 1, with a dark area 24 caused by the stop element 20.

The apparatus 10 further comprises a scanning device 26. The scanning device 26 may be a scanning polygon or rotatable polygonal mirror, with a plurality of reflecting sides 28 with mirror surfaces. The number of sides 28 may for instance be ten, as in FIG. 1. The scanning device 26 is arranged to be rotated, and a motor (not shown) for rotating the scanning device 26 may also be included in the apparatus 10. The scanning device 26 is arranged to receive the radiation 16b having passed the aperture 18, and redirect such radiation via one of the sides 28 towards the matter 12 to be inspected. No radiation 16a will reach the scanning device 26 due to the stop element 20. Instead, the dark area 24 caused by the stop element 20 will be projected via said one side 28 onto the matter 12.

The apparatus 10 may further comprise or have associated therewith a conveyor with a conveyor belt (not shown) provided below the scanning device 26. An exemplary conveying direction is indicated by arrow 30 in FIG. 1. The conveyor serves to convey matter 12 to be inspected past the apparatus, and the conveyor (belt) may be substantially as wide as the scanning or inspection width indicated by 32 in FIG. 1.

The apparatus 10 further comprises an optical detection device 34. The detection device 34 may for instance be a camera or a spectrometer. The detection device 34 has a field of view (FOV) 36 that (substantially fully) coincides with the projected dark area 24 on the matter 12 (that is, the "projected" FOV 36 is inside the dark area 24). In other words, the detection device 34 sees or is aimed towards the dark area 24, via the scanning device 26.

Figure 3:
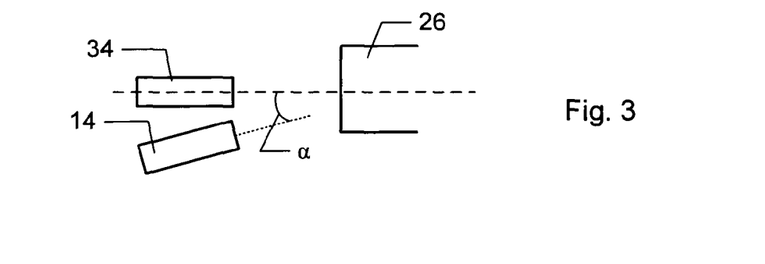
FIG. 3 is a schematic partial top view of the apparatus in FIG. 1.

The emitting device 14 may be obliquely arranged (directed) at an angle α relative to a vertical plane (=the scanning plane of the scanning device 26), as illustrated in the top view of FIG. 3, whereas the detection device 34 may be arranged or directed in the vertical plane, as seen in FIG. 1b to the right. This may facilitate placement of the devices 14, 34 in the apparatus 10, since they will not get in the way of each other.

Figure 4:
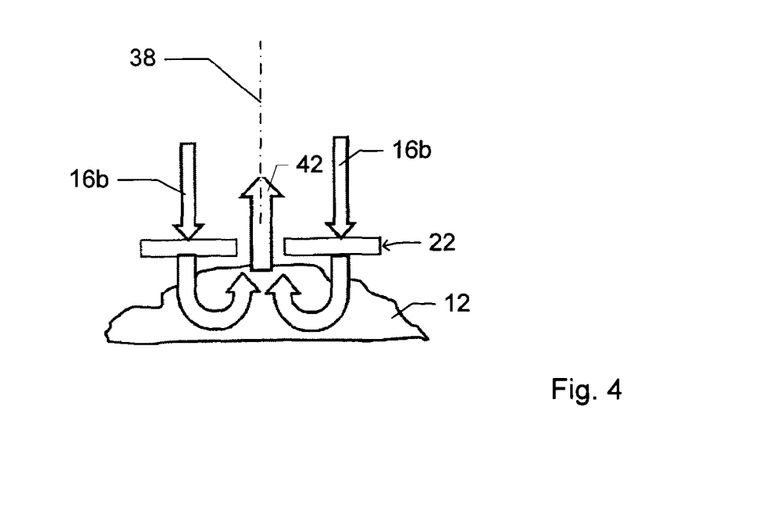
FIG. 4 illustrates transflection in an inspected matter.

Upon basic operation of the apparatus 10, radiation is emitted by the emitting device 14. A portion 16a of the radiation is stopped by the stop element 20, while other portions 16b of the radiation are allowed to pass through the aperture 18. The radiation 16b having passed the aperture 20 is redirected towards the matter 12 to be inspected by one of the reflecting sides 28 of the scanning device 26. Incoming radiation towards the matter 12 is hence indicated by 16b in FIG. 4. The projected aperture 22 is also shown in FIG. 4. At least some of the incoming radiation or light 16b enters the top surface of the matter 12, is scattered within the matter 12, and passes out of the matter 12 as scattered radiation (transflection signal). At least some of the scattered radiation will exit the matter 12 in the direction 38. This scattered radiation 42 is viewed or detected by the detection device 34. The scattered radiation 42 will depend on quality and/or composition etcetera of the inspected matter 12, allowing the apparatus 10 to determine the quality and/or composition etcetera of the inspected matter 12 based on the scattered radiation 42 detected by the detection device 34. Due to the stop element 20 and the corresponding placement of the detection device 34, no radiation reflected by the surface of the matter 12 will be received by the detection device 34. Further, any height variation of the matter 12 is not critical with respect of surface reflection, as appreciated from the projected aperture 22 at height $H_0$ and the projected aperture 22' at height $H_1$ in FIG. 1, wherein the detection device's FOV 36 is moving inside the blocked area 24. The movement of the FOV 36 as a function of height H can also be seen in particular in FIG. 1a. At height $H_2$ (FIG. 1a), the FOV 36' has moved to another position within the blocked area 24 compared to the position of FOV 36 at height $H_0$, since the emitting device 14 is obliquely arranged relative to the vertical plane. Further, no optical lens for focusing the scattered radiation towards the detection device is necessary nor present. Further, the scanning device 26 rotates, causing the projected aperture 22 and the FOV 36 to repeatedly sweep from one end of inspection width 32 to the other. This allows for of a rather wide inspection zone.

The apparatus 10 may further comprise at least one calibration element. Such a calibration element may be provided on one of the sides 28 of the scanning device 26 instead of the mirror surface, as indicated by 44 in FIG. 1. The apparatus 10 may for instance comprise one white calibration element 44 and one spectral calibration element 46 arranged on opposite sides of the scanning device 26. Such a configuration balances the weight of the scanning device 26.

Figure 5:
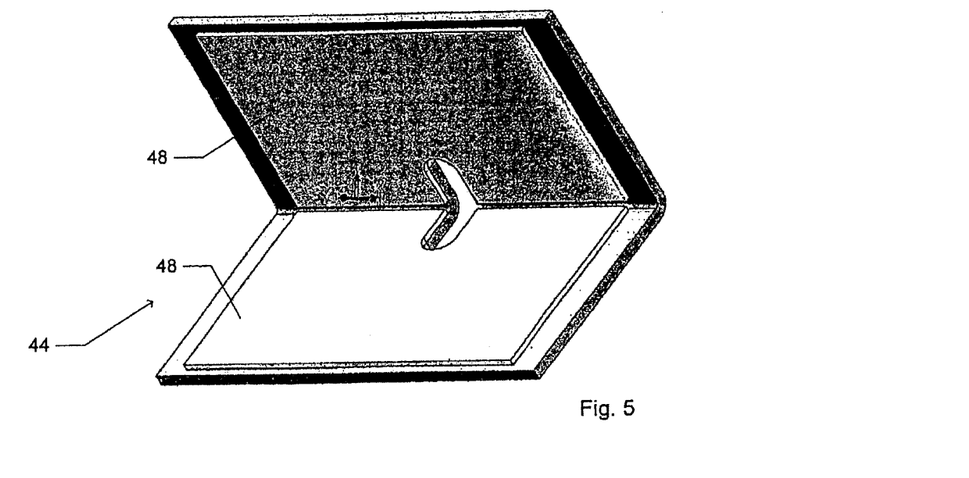
FIG. 5 is a perspective view of an example of a white calibration element.

An example of a white calibration element 44 is shown in detail in FIG. 5. The white calibration element 44 includes at least one substantially white surface, namely two white reference tiles 48 provided at about 90 degrees in relation to each other, basically forming a V-shape. Upon operation of the apparatus 10, radiation 16b having passed the stop 20 is reflected by one of the white tiles 48 towards the other, and vice versa, allowing the detection device 34 to directly receive or detect the reflected white or whitish radiation, without the radiation passing the matter. To this end, the detection device 34 may be automatically calibrated for each rotation of the scanning device 26, in order to account for any change in emission characteristics of the emitting device 14 over time.

Figure 6:
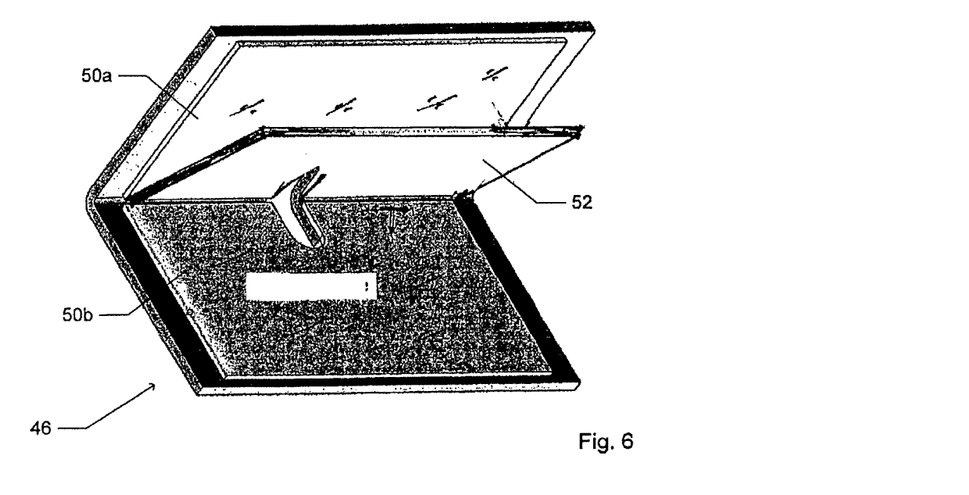
FIG. 6 is a perspective view of an example of a spectral calibration element.

An example of a spectral calibration element 46 is shown in detail in FIG. 6. The spectral calibration element 46 includes two reflecting surfaces angled in relation to each other, namely two mirror surfaces 50a and 50b provided at about 90 degrees (orthogonal) in relation to each other. Between the two mirror surfaces 50a and 50b, there is provided a transmission object 52. The transmission object 52 may be a plate arranged at about 45 degrees to each mirror surface 50a and 50b. The transmission object 52 has a particular spectral signature. The transmission object 52 may for instance be a transparent polymer. Upon operation of the apparatus 10, radiation 16b having passed the stop 20 is reflected by one of the mirror surface 50a through the transmission object 52 and towards the other mirror surface 50b, and vice versa. When passing the transmission object 52, the radiation is "coded" by the particular spectral signature (e.g. particular wavelengths), which may be directly received or detected by the detection device 34 without passing the matter. To this end, the detection device 34 may be automatically function checked for each rotation of the scanning device 26. That is, if the particular spectral signature is not detected as expected, then the detection device 34 may not function properly. This may be indicated or alerted to an operator of the apparatus 10, who then can initiate a fault localization procedure.

Figure 7:
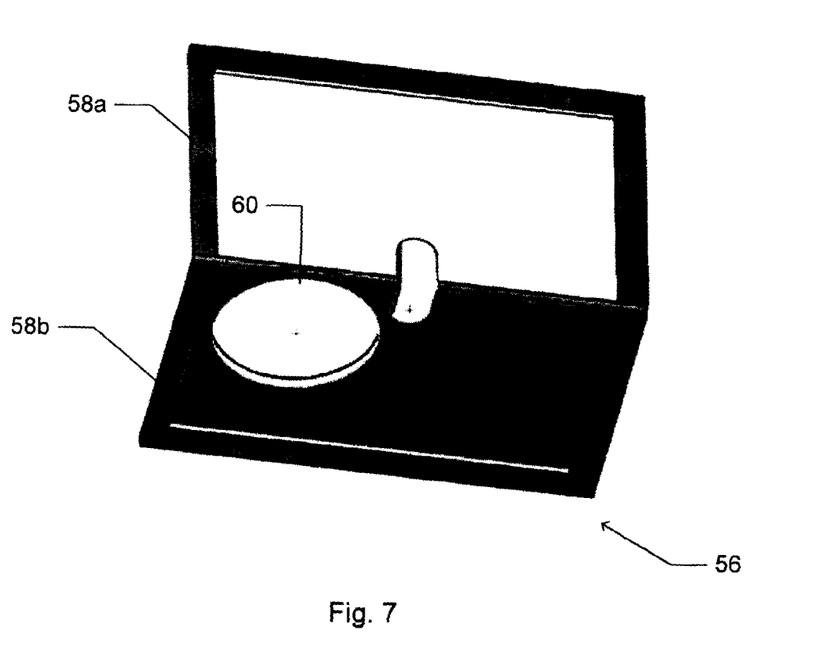
FIG. 7 is a perspective view of another example of a spectral calibration element.

Another example of a spectral calibration element 56 is shown in FIG. 7. The spectral calibration element 56 includes two reflecting surfaces angled in relation to each other, for example two mirror surfaces 58a and 58b provided at about 90 degrees (orthogonal) in relation to each other. On one of the surfaces, there is placed a transmission object 60 in the form of a circular element. The transmission object 60 has a particular spectral signature, and the spectral calibration element 56 may function in a similar manner as the spectral calibration element 46 of FIG. 6.

Also black calibration may be provided in the apparatus 10. For instance, the interface 54 (e.g. a gap) between the sides 28 of the scanning device 26 may cause short period of time where no radiation is scanned along the inspection width 32 even when the scanning device 26 is rotating, and the detection device 34 may be configured to take a reading during this period to perform black calibration.

Figure 8A:
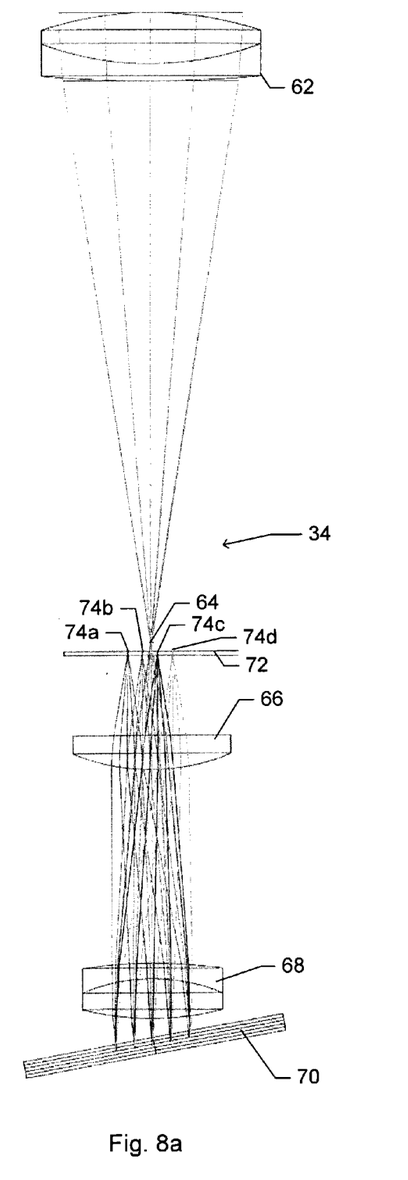
FIG. 8a is top view of a detection device that may be used in the present apparatus.
Figure 8B:
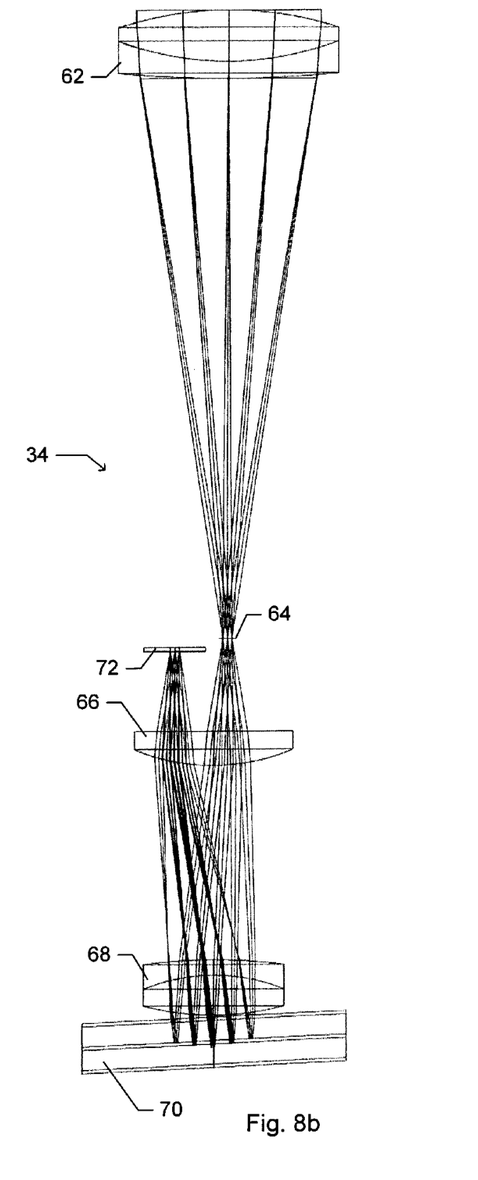

An exemplary detection device 34 that can be used in the present apparatus 10 is shown in more detail in FIGS. 8a-8b. The detection device 34 comprises, in sequence: an objective lens 62, a slit 64, additional lenses 66 and 68, and a grating 70. 66 together with 68 may be collimating lenses, and the lens 66 could be omitted for lower resolution. Further, the detection device 34 comprises a detector array 72, which is placed almost above the slit 64. Upon operation, incoming light is focused by the objective lens 62 to pass through the slit 64. The light then passes the additional lenses 66 and 68 to the grating 70. The grating 70, which is two-dimensionally tilted with respect to the incoming light, splits the light into several beams travelling in different directions according to color. The various color channels are then focused by the additional lenses 66 and 68 onto the detector array 72. In FIG. 8a, the different positions 74a-d on the detector array 72 may correspond to blue, green, red, and yellow, respectively. Hence, if radiation is detected at position 74a, this indicates that the radiation includes blue. The exemplary detection device 34 of FIGS. 8a-8b has less lens elements than a standard spectrometer, and results in less cost and increased signal.

Figure 9:
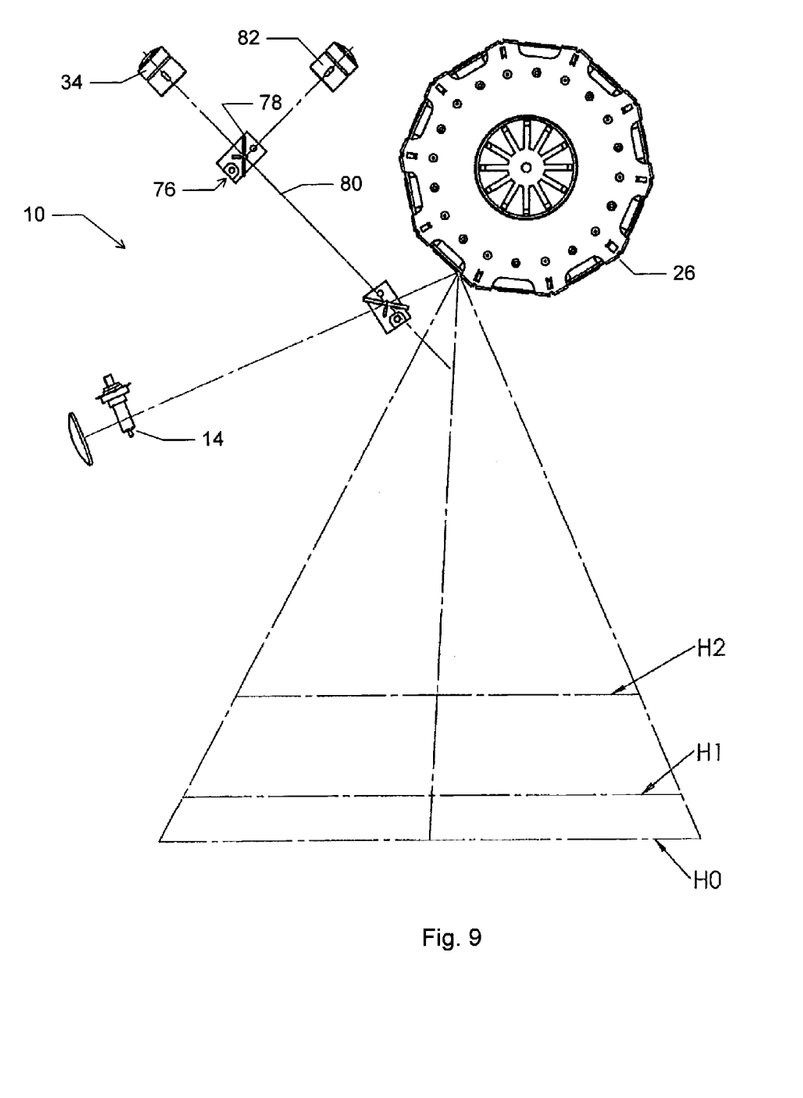
FIG. 9 is a side view of an apparatus for inspecting matter according to another embodiment of the present invention.

FIG. 9 shows an alternative embodiment of an apparatus 10' for inspecting matter according to the present invention. The apparatus 10' is similar to the previously described apparatus 10, but comprises a beam splitter 76 arranged in a beam path between the scanning device 26 and the detection device 34. The beam splitter 76 comprises an reflecting/transmitting element 78 which may be arranged at an angle of about 45° with respect to incoming radiation 80. The element 78 may for example be adapted to transmit 800-1100 nm (near-infrared, NIR) and send it towards the detection device 34, and to reflect 400-700 nm (visible light) and send it to another detection device 82 of the apparatus 10'. The beam splitter 76 can also be arranged to be tilted for increasing or decreasing said angle, such that the detection device 82 (which receives light reflected by element 78) receives reflected light from the projected aperture 22 rather than transflected light. In other words, the detection device 82 sees or is aimed towards an area of the projected aperture 22 apart from the dark area 24, via the scanning device 26 and element 78. The detection device 34, which receives light transmitted through element 78, is not affected by the tilting of the beam splitter 76, and still detects transflected radiation from the dark area 24.

Applications of the present apparatus 10 and 10' include, but are not limited to, inspecting matter 12 such as meat, chicken, and/or fish for organic nutrients such as carbohydrates, fats, proteins (or their building blocks, amino acids), and vitamins.

It should be noted that the various calibration elements could be used also in applications or apparatuses without the stop element 20.

The person skilled in the art will realize that the present invention by no means is limited to the embodiment(s) described above. On the contrary, many modifications and variations are possible within the scope of the appended claims.

The invention claimed is:

1. An apparatus for inspecting matter, the apparatus comprising:
   an emitting device adapted to emit radiation;
   a stop element adapted to block some of the radiation emitted by the emitting device;
   a scanning device adapted to project a dark area caused by the stop element on the matter, and to redirect radiation having passed the stop element towards the matter, wherein at least some of the redirected radiation is scattered within the matter and passes out of the matter as scattered radiation; and
   a detection device adapted to receive or detect the scattered radiation via the scanning device, wherein the detection device's field of view coincides with the projected dark area.

2. An apparatus according to claim 1, wherein the stop element is provided in front of the emitting device.

3. An apparatus according to claim 1, wherein said stop element is provided in an aperture placed in front of the emitting device.

4. An apparatus according to claim 1, wherein the emitting device and the detection device are obliquely arranged in relation to each other.

5. An apparatus according to claim 1, wherein the scanning device is adapted to sweep the projected dark area, the redirected radiation, and the field of view of the detection device along an inspection width where matter to be inspected may be present.

6. An apparatus according to claim 1, wherein the scanning device is a rotatable polygonal mirror having a plurality of sides.

7. An apparatus according to claim 6, wherein at least one side of the rotatable polygonal mirror comprises a calibration element.

8. An apparatus according to claim 7, wherein said calibration element is one of:
- a white calibration element comprising at least one substantially white surface angled for allowing the detection device to directly receive or detect radiation reflected by the substantially white surface(s); and
- a spectral calibration element including two reflecting surfaces angled in relation to each other and with a transmission object provided there between, the transmission object having a particular spectral signature.

9. An apparatus according to claim 7, comprising two such calibration elements arranged on opposite sides of the rotatable polygonal minor.

10. An apparatus according to claim 1, further comprising a conveyor adapted to convey matters to be inspected.

11. An apparatus according to claim 1, further comprising a beam splitter arranged in an optical path between the scanning device and the detection device, wherein the beam splitter is adapted transmit some of the radiation incoming towards it to the detection device and to reflect some of the incoming radiation to another detection device.

12. An apparatus according to claim 11, wherein the beam splitter is tilted or tiltable, such that the another detection device may receive radiation reflected by the matter.

13. Method for inspecting matter, which method comprises:
- providing the apparatus of claim 1,
- emitting radiation by means of the emitting device;
- blocking some of the emitted radiation by the stop element provided in front of the emitting device;
- projecting with the scanning device a dark area caused by the stop element on the matter,
- redirecting radiation having passed the stop element towards the matter, wherein at least some of the redirected radiation is scattered within the matter and passes out of the matter as scattered radiation; and
- receiving or detecting with the detection device the scattered radiation via the scanning device, wherein the detection device's field of view coincides with the projected dark area.

14. An apparatus according to claim 1, wherein reflected radiation is not received by the detection device.

* * * * *